United States Patent
Besson et al.

(10) Patent No.: US 6,719,706 B2
(45) Date of Patent: Apr. 13, 2004

(54) METHOD FOR IDENTIFYING PHYSIOPATHOLOGICAL PARAMETERS THAT CHARACTERIZE THE LOWER URINARY TRACT

(75) Inventors: Gilbert R Besson, Montgeron (FR); Pierre P Nelson, Montreuil (FR); Francoise A Valentini, Montreuil (FR)

(73) Assignee: Laborie Medical Technologies Corp., Williston, VT (US)

( * ) Notice: Subject to any disclaimer, the term of this patent is extended or adjusted under 35 U.S.C. 154(b) by 0 days.

(21) Appl. No.: 10/216,198

(22) Filed: Aug. 12, 2002

(65) Prior Publication Data

US 2003/0097039 A1 May 22, 2003

Related U.S. Application Data (60) Provisional application No. 60/311,364, filed on Aug. 13, 2001.

(51) Int. Cl.$^7$ .................................................. A61B 5/00
(52) U.S. Cl. ...................................................... 600/561
(58) Field of Search .............................. 600/561, 595, 600/373, 546, 300, 435; 604/915, 102.01, 21, 920; 424/94.2, 94.21, 94.6, 94.61, 94.62, 94.63, 94.64, 94.65, 94.67

(56) References Cited

U.S. PATENT DOCUMENTS

| | | | | | |
|---|---|---|---|---|---|
| 4,063,548 A | * | 12/1977 | Klatt et al. | .................. | 600/546 |
| 4,538,621 A | * | 9/1985 | Jarczyn | ....................... | 600/561 |
| 5,116,615 A | * | 5/1992 | Gokcen et al. | ............. | 424/94.2 |
| 5,331,548 A | * | 7/1994 | Rollema et al. | ............. | 600/561 |
| 5,617,876 A | * | 4/1997 | van Duyl | .................... | 600/595 |
| 6,447,462 B1 | * | 9/2002 | Wallace et al. | ............. | 600/561 |

* cited by examiner

Primary Examiner—Max F. Hindenburg
Assistant Examiner—Brian Szmal
(74) Attorney, Agent, or Firm—Sherman & Shalloway (57) ABSTRACT

A method for identifying and analyzing physiopathological parameters that characterize the condition of the lower urinary tract in patients in which computer generated theoretical urodynamic flow curves are generated, manipulated and compared with curves based on measured flow data for the patient. The method provides a means to determine the physiological condition of a patient without resort to, or with only minor, invasive techniques.

10 Claims, 11 Drawing Sheets

Detrusor pressure:
  dashed: recorded
  continuous: calculated

Vu (meas)=355 Vu (calc)=329 Vr(calc)=26 pucp=22 bncp=0

FIG. 5B

Flow curve:
  dashed: recorded
  continuous: calculated

Detrusor pressure:
 dashed: recorded
 continuous: calculated

FIG. 6A

Flow curve:
 dashed: recorded
 continuous: calculated

Vu (meas)=355 Vu (calc)=336 Vr(calc)=19 pucp=50
bncp=50 Detrusor force coefficient=2.10

Fitting first pucp=bncp

FIG. 9A

Fitting then bncp with pucp=30. We try bncp=30,35 and 40.
The best value is bncp=38 cm H2O.

A gradual optimization process to determine
the value of each physiopathological parameter

*Flow and pressure recorded curves*
*Urethral catheter diameter*

Compare with normal micturition
Give the value for normal subjects to all the parameters Search for the best value of pucp fitting the plateau of the flow curve
with normal nervous excitation and normal detrusor force Search simultaneously the best values of pucp and of the detrusor force coefficient
fitting both the plateau of the flow and the pressure curves
(In case of free flow examination, go to the next entry)

Search the bladder neck counter-pressure bncp and/or the bladder neck
excitation shaping the beginning of the curves

Search for a possible fall of the detrusor excitation, then for a possible final
effective abdominal pressure shaping the end of the curves

FIG. 10

Fitting the recorded curves of figures 4-7 by the model

FIG. 11A

Fitting the recorded curves by an urethral resistance approximation

FIG. 11B

METHOD FOR IDENTIFYING PHYSIOPATHOLOGICAL PARAMETERS THAT CHARACTERIZE THE LOWER URINARY TRACT

CROSS REFERENCE TO RELATED APPLICATION

This application claims the benefit of U.S. Provisional Application No. 60/311,364, filed Aug. 13, 2001.

FIELD OF THE INVENTION

The present invention is directed to a method for identifying and analyzing the physiopathological parameters that characterize the condition of the lower urinary tract in patients whereby actual and theoretical urodynamic flow curves are compared and evaluated to provide a non-invasive and direct evaluation of the evolution of a particular disease or of the effectiveness of a treatment regimen.

BACKGROUND OF THE INVENTION

Diseases of the lower urinary tract system can produce voiding anomalies which are measured during a urodynamic examination. Such examinations measure and record the evolution of hydrodynamic magnitudes, i.e., flow rate, pressure and volume of fluid, during a urination cycle. More often than not, the curves recorded by such examinations are too complicated for rapid and summary use and do not provide anything more than a general indication of conditions which must then be refined by invasive procedures, such as visual examination by urethroscope, or by use of X-ray, MRI or the like.

SUMMARY OF THE INVENTION

The present method provides a means to precisely and quantitatively identify the functional status of the lower urinary tract of a patient, whether male or female. It provides a non-invasive means to confirm or overrule a clinical diagnosis, or to track the evolution of a disease. The method uses a computer generated comparison between a urodynamic flow curve and a pressure curve recorded during micturition and theoretical models based on seven physiological parameters that together describe the lower urinary tract of an individual in good health. By applying the theoretical curves to the recorded curves, one can determine how far from ideal a particular individual is. In addition, by modifying the values from which the theoretical curves are calculated, one can bring the theoretical curves into coincidence thereby making it possible to identify those physiopathological parameters that are disturbed in a particular patient.

The values that are measured during a urodynamic procedure characterize the status of the lower urinary tract of which each elementary anomaly, e.g., urethral stenosis, is associated with a particular parameter, in this example, reduction of the urethral cross section. Each parameter is, in turn, associated with a physiological significance, the numeric value of which characterizes the magnitude of the phenomenon. These values vary according to the evolution of the particular disease or the effectiveness of the treatment therefor.

DETAILED DESCRIPTION OF THE INVENTION

Figure 1:
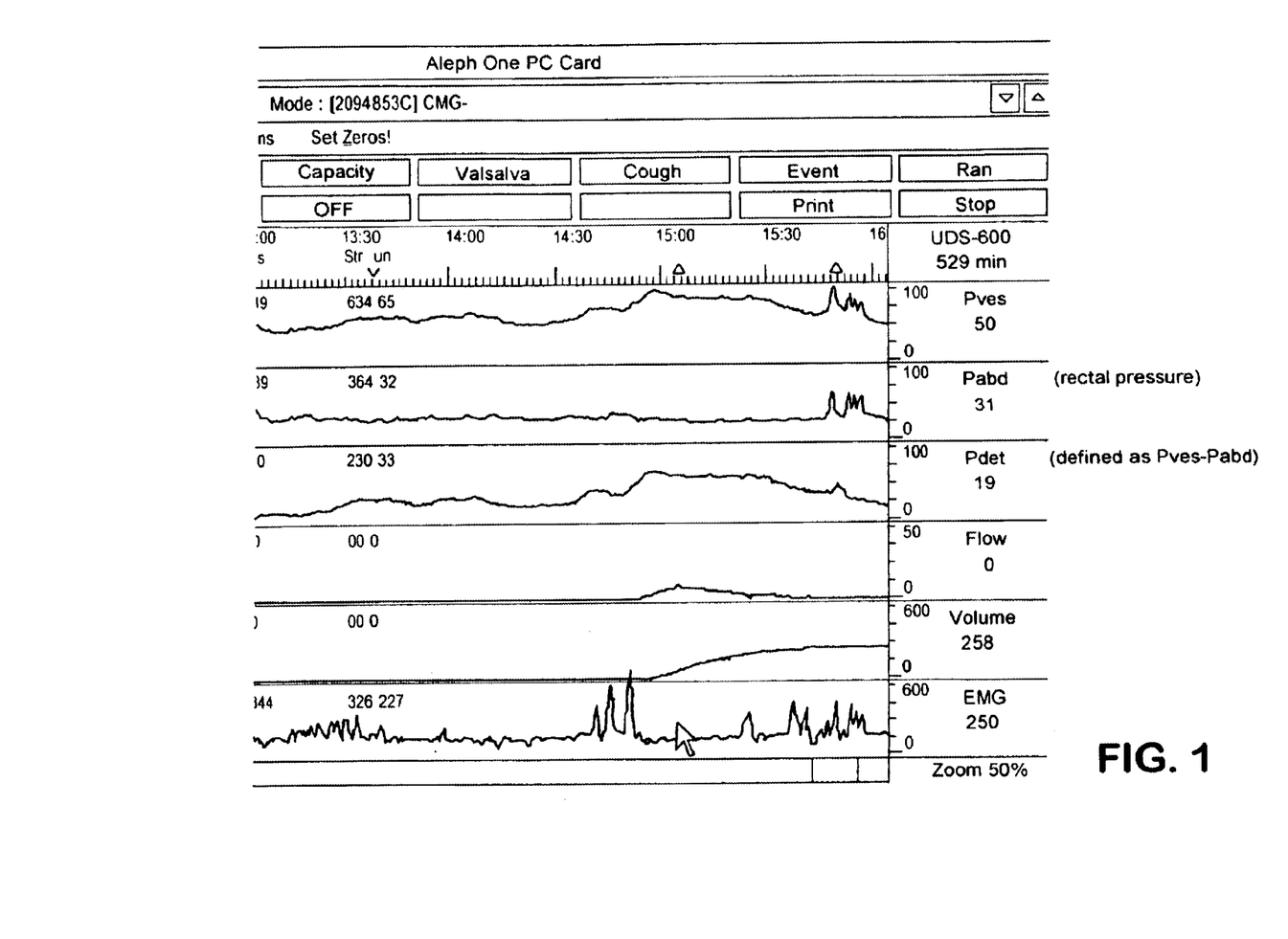
FIG. 1 is a screen from a urodynamic monitor showing measured values for intravesical pressure, abdominal pressure, detrusor pressure, flow rate and volume.

During a urodynamic examination, the flow rate, Q, intra-vesical pressure, Pves, abdominal or rectal pressure, Pabd, and the actual volume of urine voided, V, are measured. Typically, these measurements are taken using a unit such as the Aquarius® urodynamic monitor and processor available from Laborie Medical Technologies, Corp. of Williston, Vt. From these values the detrusor pressure, Pdet, is determined as the difference between the vesical and the abdominal pressures, Pdet=Pves−Pabd. FIG. 1 shows a typical screen image from an Aquarius® unit illustrating the charts for these values which are converted to the measured urodynamic curves for Pves, Pdet and Pabd in FIG. 2 and flow rate Q in FIG. 3. These are the recorded curves directly associated with the physiopathological parameters of the patient.

The method of the present invention applies a theoretical or mathematical model based on physiopathological parameter values to the recorded curves in order to make a quantitative determination of the functional status of the patient's lower urinary tract without resorting to invasive procedures. The method proceeds with successive iterations of the calculated or theoretical curve leading to a coincidence with the recorded curve that characterizes the functional status of the patient's lower urinary tract. If necessary, the parameter values of the theoretical curve are corrected until the coincidence of the recorded and theoretical curves has an error of less than 1% over the curve area.

The theoretical model is based on characteristics for an individual in good health and describes the following parameters:

1) The geometry and the contractile, elastic and visco/elastic properties of the bladder,
2) The geometry and the contractile and elastic properties of the bladder neck,
3) The geometry and elastic properties of the urethra from the bladder neck to the urinary meatus, 4) The geometry of the contractile properties of the sphincters,
5) The variation over time of the nervous excitation of the detrusor (bladder muscle),
6) The variation over time of the nervous excitation of the sphincters, and
7) The effect of the perineal muscles.

This description is based on an extensive collection of data which has made it possible to determine the nature of the physiological parameters that are most frequently found in well-defined pathologies. Providing the description as a set of numbers, functional relationships and differential equations, permits the values for particular phenomena in the description to be modified so that the model can be used to simulate any anomaly. Furthermore, the data can be manipulated via a computer program to make rapid calculations and produce theoretical curves that can be directly superimposed over the measured curves on the urodynamic monitor for direct comparison and determination of the particular physiological parameters of a patient without resort to invasive or extensive monitoring procedures.

Since the flow of urine in the urethra follows aerodynamic principles, equations and methods for calculating supersonic flows can be transposed to the calculation of the urine model. Applying the output of the calculations to a computerized graphic generator, makes it possible to read the numeric values in the manner of a urodynamic flow curve and to compare a theoretical or calculated curve with an actual recorded or measured curve from a particular patient. By modifying the values for the theoretical curve, it can be brought into coincidence with the measured curve and the values that are modified together with the degree of such modifications is characteristic of the particular physiopathological condition exhibited by the recorded curve. The use of a graphic display also makes it possible to display and compare both actual and theoretical curves for related specific physiopathological parameters, such as the detrusor pressure, as well as to change the representation method such as urinary flow rate as a function of pressure, or by variation of the longitudinal section of the bladder/urethra during urination.

The calculations made to produce the theoretical curves are done automatically as part of the operation of the urodynamic monitor. As such, the mathematical functions are preferably part of the operational software of the urodynamic monitor and are readily manipulatable through the normal interface means of a computer.

The theoretical calculations are made in accordance with the following values and formulas.
The Bladder:
Properties of a strip of detrusor muscle:

Structure of the detrusor: $F=Fe+Fc=Fve$
where Fc is the contractile force, Fe is the elastic force, Fve is the viscoelastic force and F is the total force along a strip L of detrusor where L is the length of the strip and $L=17.75lc+4.25lve=5.26le+2.736lve$ where lc is the relative length of the contractile element, le is the relative length of the elastic element and lve is the relative length of the viscoelastic element and $1<le$ and $lve \leq 5$, $lc<0$.

Collapse restriction:
If the above equations lead to $lc<0$ or $le<1$, then Fc or Fe=0.
Elastic elements:
$Fe=0.865\Phi(le)/\Phi(3)$ with $\Phi(y)=K(y/5)-y^{-1}K(0.2y^{-0.5})$
Viscoelastic elements:
$Fve=1.68\Phi(\lambda)/\Phi(3)$ and $dlve/dt=(\lambda-lve)/\tau$ with $\tau=300s$
Contractile elements:
$Fc=\phi L \phi V \phi E$ (length, velocity, excitation depending factors) where:
$\phi L=14exp\alpha(1-exp\beta)$ with $\alpha=-2.57(1-lc)^2$ and $\beta=-61c$
$\phi V=exp\chi$ with $\chi=-0.2LQ/V+Vc)$
$\phi E=5\epsilon/(4\epsilon+1)$ with $\epsilon=(E_D^2/(1+E_D)(3+E_D))^2$
Properties from the strip to the whole bladder:
Where Pves=intravesical pressure (cm $H_2O$), Peff=effective abdominal pressure, (as distinguished from Pabd)
Q=mass flow rate, V=actual volume, V0=theoretical maximum volume and Vc=mean muscular volume, the relationships are as follows:
$(L/40)^3=(V+Vc)/(V0-Vc)$ with $V0=2500$ cm$^3$ and $Vc=0.016V0$
$Q/V=(3/L)dL/dt$ and $Pv=Peff+4118F/L^2$.
The urethra:
Where x=the abscissa along the urethra (x=0 at the bladder neck), P(x, t) is the pressure of fluid at x abscissa and time t, Pwall is the pressure due to the elasticity of the wall of the urethra, Pout is the pressure from outside elements, Psph is the pressure due to the sphincters (for a normal subject without compressive obstruction, Pout=Psph), A(x, t) is a section of the fluid flow and $E_s$ is the excitation of the sphincters, the relations are as follows:
Pressure-section relations:
$A(x, t)=\sigma(x)G(Pwall)$ and $Pwall(x, t)=P-Pout$.
The sphincters:
$Psph(x, t)=Pmax(x)\phi E(t)$ where $\phi E=5\epsilon(4\epsilon+1)$ with $\epsilon=(E_S^2/(1+E_S)(3+E_S))^2$ For a female: $Pmax = 35.92x(3.5 - x)$ if $0 < x < 3.5$ cm
$= 0$ if $3.5 < x < 4$ For a male: $Pmax = 30$ if $0 < x < 3.5$
$= -580 + 253.45x - 22.62x^2$ if $3.5 < x < 8$
$= 0$ if $8 < x < 17$.

The shape factor of the urethra:
For a male: $\sigma(x)=0.2\delta^2$ cm2 ($0<x<17$ cm) where $\delta$ is given by the following Table 1.

| x | 0 | 1 | 2 | 3 | 4 | 5 | 6 | 7 | 8 | 9 | 10 | 11 | 12 to 17 |
|---|---|---|---|---|---|---|---|---|---|---|----|----|----------|
| δ | 3.5 | 2 | 3.3 | 2.9 | 1.4 | 1.45 | 1.25 | 1 | 1.75 | 2.5 | 2.5 | 1.5 | 1 |

For a female: $\sigma(x)=0.3\delta^2$ cm2 ($0<x<4$ cm) where $\delta$ is given by the following Table 2.

| x | 0 | 0.5 | 1 to 4 |
|---|---|-----|--------|
| δ | 2.86 | 1.23 | 1 |

Along the urethra:

| | |
|---|---|
| $z < 2$ cm $H_2O$ | $G(z) = 0$ |
| $2 < z < 12$ | $G(z) = 0.01902\ g_1\ (\exp g_2 - 1)$ |
| $12 < z$ | $G(z) = g_1\ (\exp g_3)$ |
| with $g_1 = 1 + (z/171.4)$ | $g_2 = (z-2)/3.014 \quad g_3 = (10-z)/2.837$ |

In the bladder neck:

| | |
|---|---|
| $z < 10$ | $G_{bn}(z) = 0$ |
| $z > 10$ | $G_{bn}(z) = g_1 \exp g_4 \quad$ with $g_4 = (10-z)/7.21$ |

Urethra and bladder neck counter-pressures:

The external pressure Pout(t) acting on the urethra is the sum of the sphincter pressure and, in the case of a compressing obstruction, of a time dependent counter-pressure: cp(t)=pucp x R(t) where pucp is the prostatic urethra counter-pressure and where R=1 if t<20s and R=0.5=0.5/(1+0.002(t−20)$^2$) if t>20s (t=0 at the start of the flow). The external on the bladder neck bncp is the sum of cp(t) and of a term due to the bladder neck excitability (bladder-bladder neck coupling): bncp(t)=cp(t)+10$^4$ B.F$_c$/r where F$_c$ is the contractile force of the detrusor, B a bladder-bladder neck coupling parameter and r the mean radius of the bladder neck given by $\pi^2$=s+0.17 cm$^2$. Here, s is the area of the fluid flow within the bladder neck.

Hydrodynamics:

The method deals with a turbulent flow, i.e., without radial dependence of the velocities and with frictional losses. Thus, p is density (p=1 g.cm$^{-3}$), v is the axial velocity of the fluid, Ptot is the total pressure and is equal to P+½pv$^2$. Q=pAv is the flow rate. Accordingly, the preservation of mass and impulse is:

$$p\partial A/\partial t + \partial Q/\partial x = 0 \quad p\partial t + \partial v/\partial P\text{tot}, \partial x + \xi pv|v|A^{-\frac{1}{2}} = 0 \text{ with } \xi = 0.0133$$

The upstream condition is calculated as Ptot(0, t)=Pv(t) Q=−dV/dt; and for the downstream condition, the pseudo sonic velocity c(x, t)=(A/p∂p/∂A)$^{1/2}$ is introduced. The flow is sonic at the most constricted point.

In accordance with the excitation versus time laws:

$$\begin{aligned} E_D &= 0 & &\text{if } t < 0 \\ &= 0.5t/(1+0.1t) & &\text{if } t > 0 \\ E_S &= 1.5 & &\text{if } t < 1.5s \\ &= 0 & &\text{if } t > 1.5 \end{aligned}$$

Figure 8:
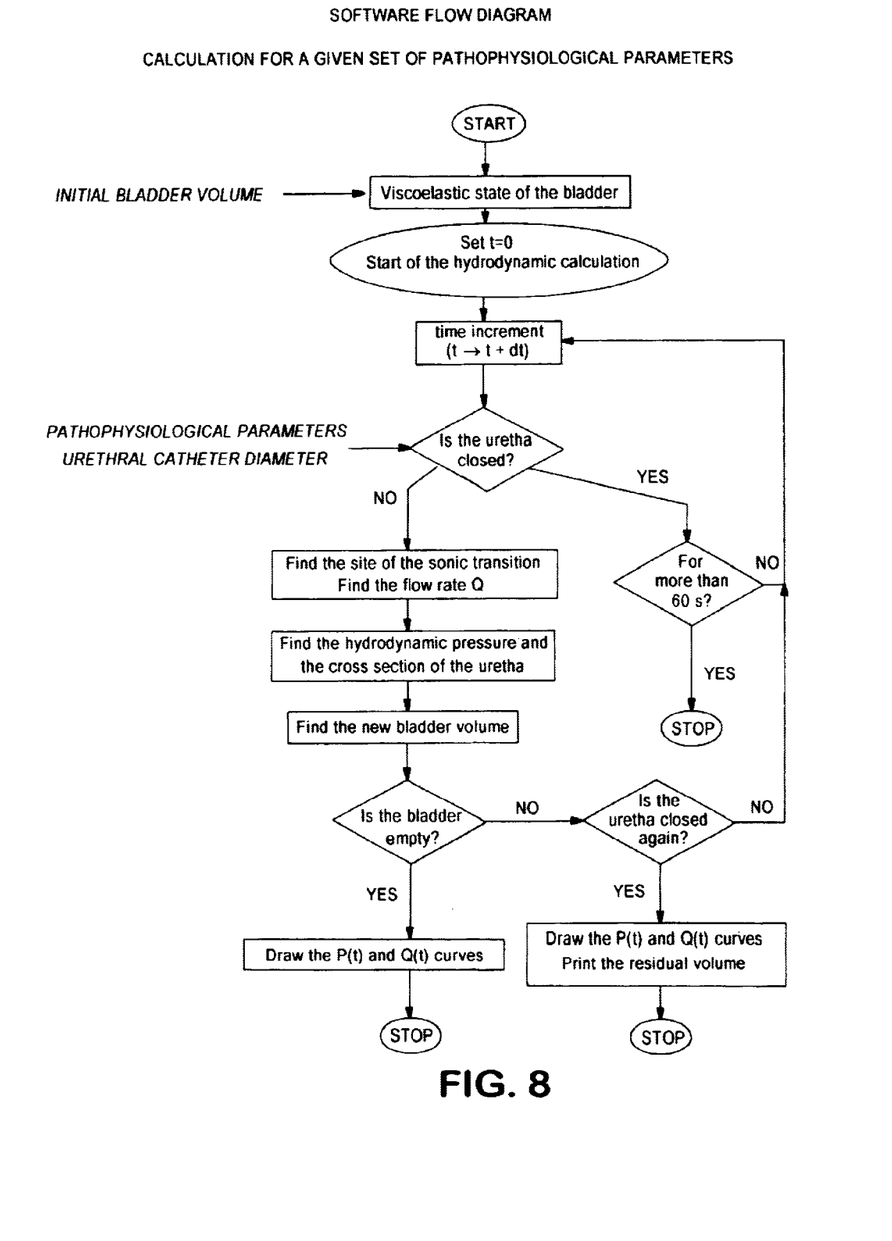
FIG. 8 is a software flow diagram for a micturition calculation.

The foregoing formulas and values are transformed by introducing convenient reduced variables (such as Q$^2$/P) and using well known methods to integrate this set of differential equations in a strongly optimized way. Although the algorithm was written in C on a Linux based operating system, it is readily translatable into any computer language for use on any current personal computer, for example a 500 MHz processor with at least 64 Mb of RAM. As shown in the software flow diagram of FIG. 8, the program calculates the visco-elastic state of the bladder at the beginning of voiding, the detrusor pressure at voiding, the flow rate, hydrodynamic pressure and cross section of the urine stream. These calculations are converted to curves for comparison with actual measured flow curves in the method.

The operation of the method will now be explained on the basis of a patient with benign prostatic enlargement with reference to the drawing figures.

A urodynamic examination is conducted on the patient using an Aquarius® urodynamic monitor and processor to measure flow rate, Q, intravesical pressure, Pves, and rectal or abdominal pressure, Pabd. These measurements are displayed digitally and graphically as shown in FIG. 1 together with the detrusor pressure, Pdet, which is calculated by the unit as the difference between the vesical and abdominal pressures, Pves−Pabd=Pdet. In addition to these values, flow and volume values are also displayed.

Figure 2:
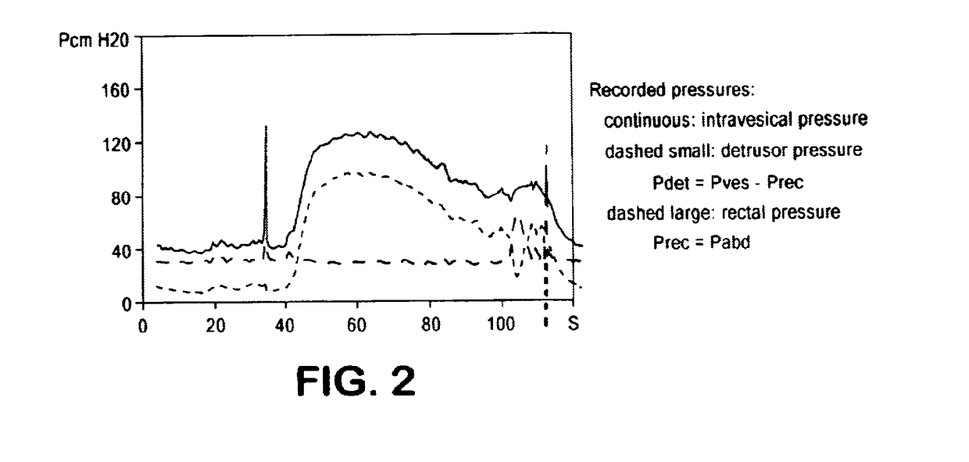
FIG. 2 shows a graph of measured intravesical pressure, abdominal pressure and detrusor pressure.
Figure 3:
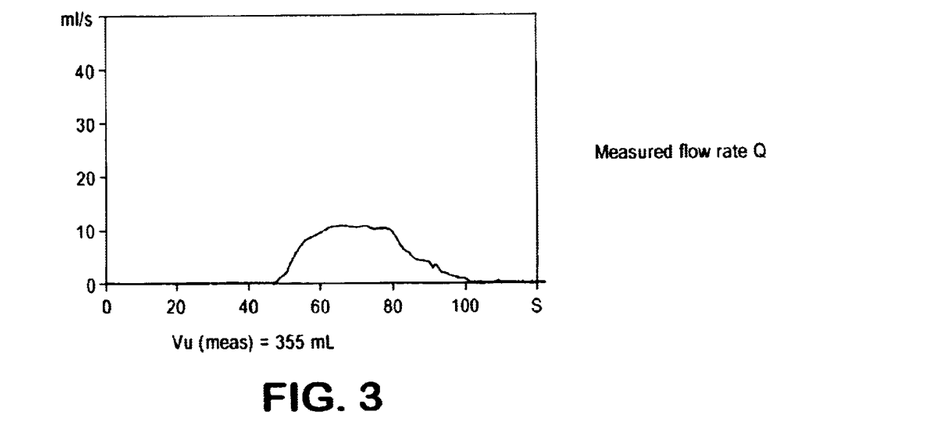
FIG. 3 shows a graph of measured flow rate

The duration of the examination is about 30 minutes with a two minute portion of data including a period of micturition that is selected and applied to calculations to produce the urodynamic curves for Pves, Pdet, and Pabd seen in FIG. 2. FIG. 3 shows the curve for the measured flow rate for the patient. In some cases (such as free flow examinations) one measures only the flow rate Q, but not the pressures.

Figure 9A:
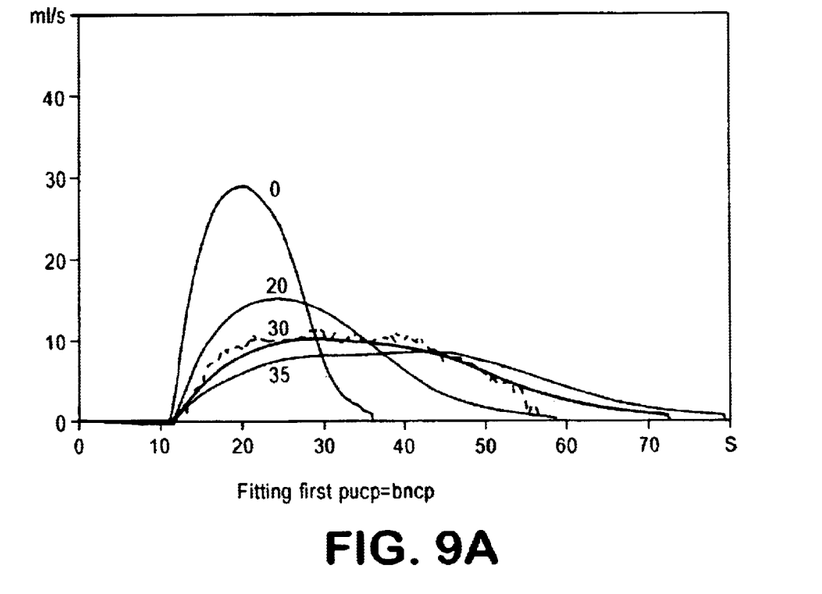
FIGS. 9A, B and C illustrate a real case example of measured values applied to the method of the present invention.
Figure 9B:
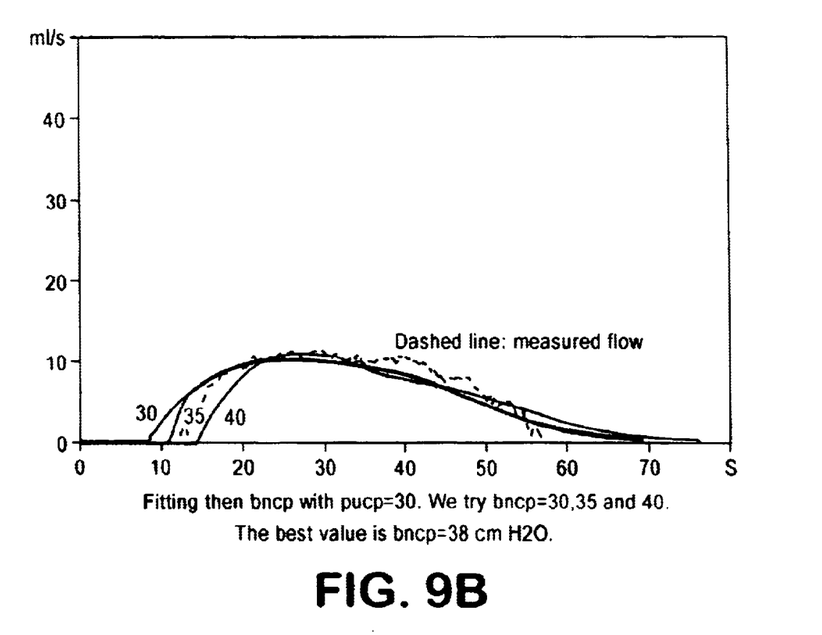
Figure 9C:
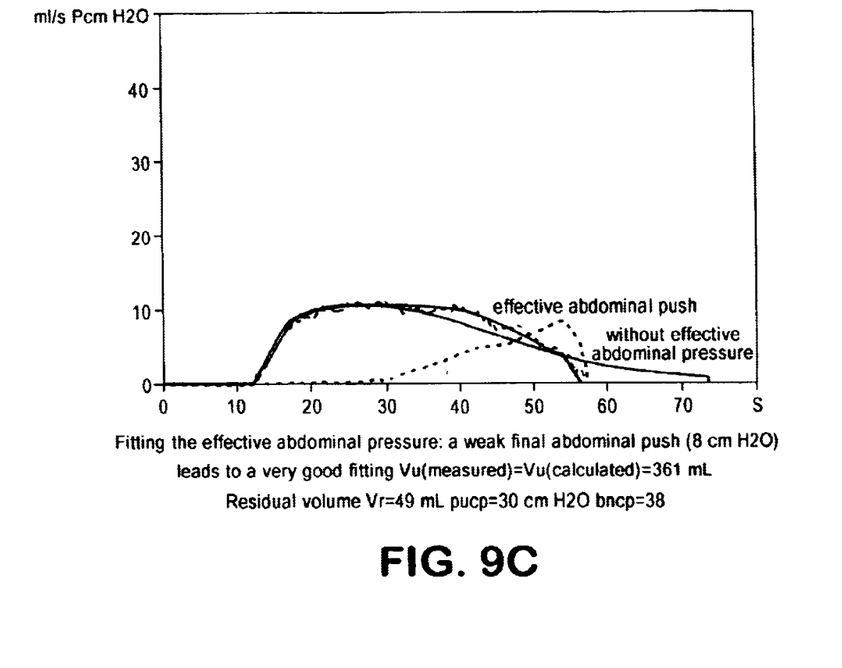
Figure 10:
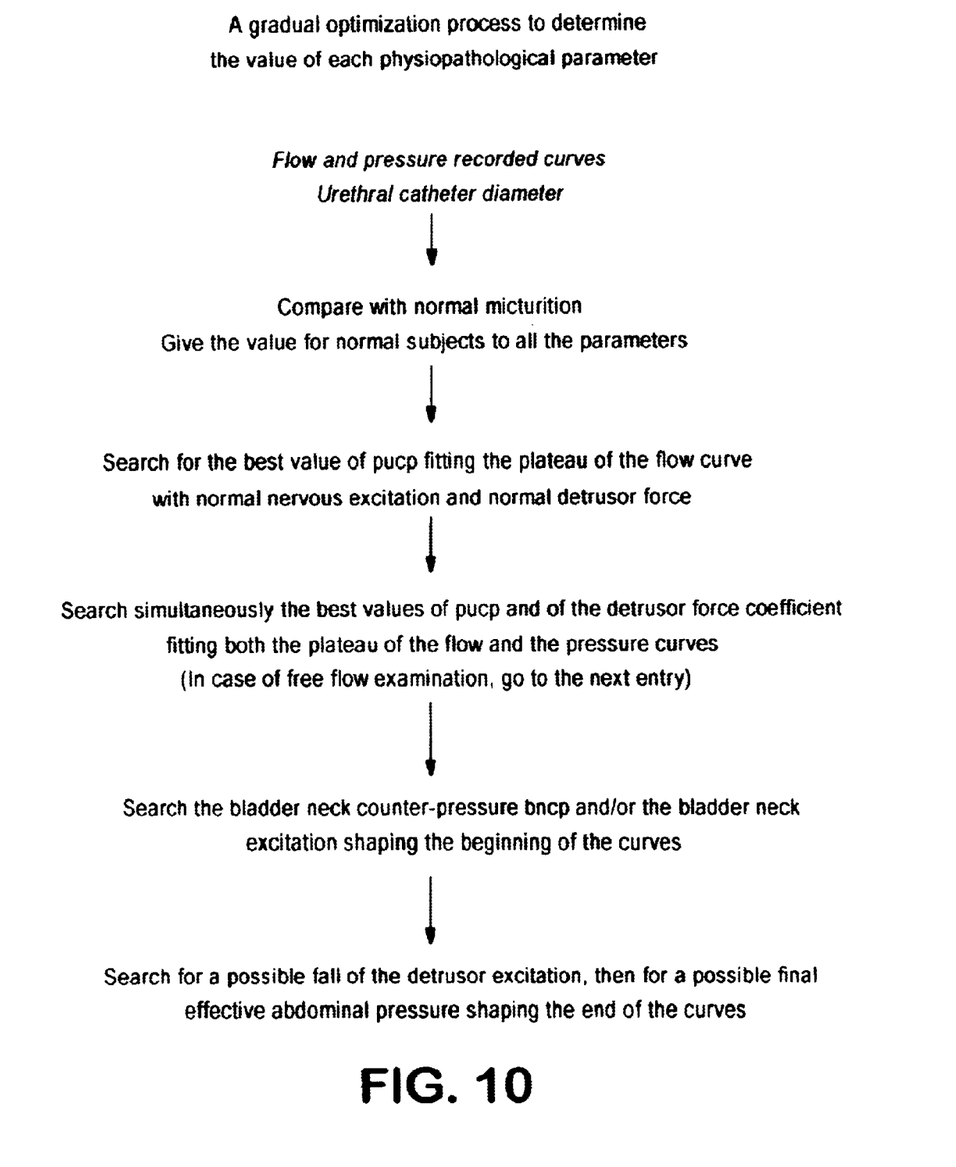
FIG. 10 is a flow diagram for the optimization process of the present invention.

The method now proceeds to the calculation of a theoretical flow rate curve and a theoretical detrusor pressure curve based on physiopathological parameters using the values and formulas described herein to produce theoretical curves equal to the measured curves thereby identifying the specific parameters causing the measured conditions. FIG. 9 shows, in the simple case of a free flow examination, how one successively determines the values of pucp and bncp by looking at the beginning of micturition and at the effective abdominal pressure. The manual or automatic gradual trial and error processing is schematized in FIG. 10. Although performing about 30 calculations, the duration of processing is less than one minute. Previously, such calculations would have to be laboriously made by hand and the curves plotted and visually compared with the actual measured curves with the result that such calculations and comparisons were not done. Instead, where a patient's measured data did not conform to normal conditions, the options for the medical practitioner were to make a guess based on knowledge and experience or to conduct invasive and extensive tests to further determine the particular physiological condition of the patient. Applying the formulas identified herein in calculation software run on a computer connected to the urodynamic monitor significantly speeds up the production of the theoretical curves and permits their ready modification by simply changing the values for the physiological parameters that are used by the calculation software. The computer then creates theoretical curves based on those values and superimposes such curves on the actual measured curves whereby a direct comparison between the theoretical and measured curves is made. This direct comparison permits the operator to readily determine the particular physiological condition responsible for the measured results. FIGS. 4–7 illustrate the manipulation of the theoretical curves by this method and their direct, on screen, comparison with the actual measured curves to determine the physiological condition of the patient.

Figure 4A:
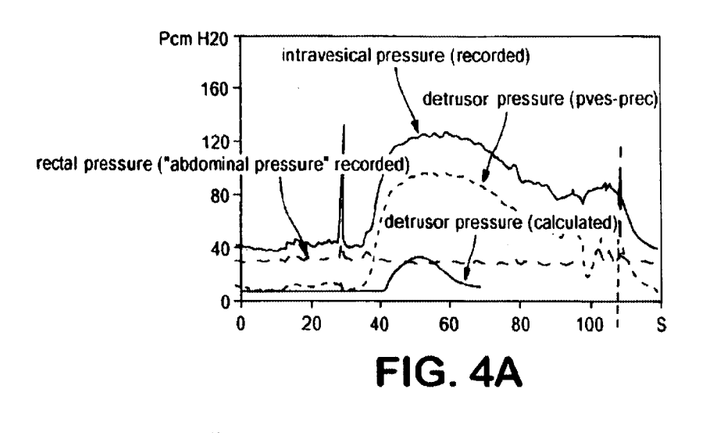
FIGS. 4A, B and C are a screen from a computer monitor showing the graphs of FIGS. 2 and 3 with the theoretical curves for detrusor pressure and flow rate calculated from the values shown and superimposed in the primary window and a secondary window for entry of parameter values.
Figure 4B:
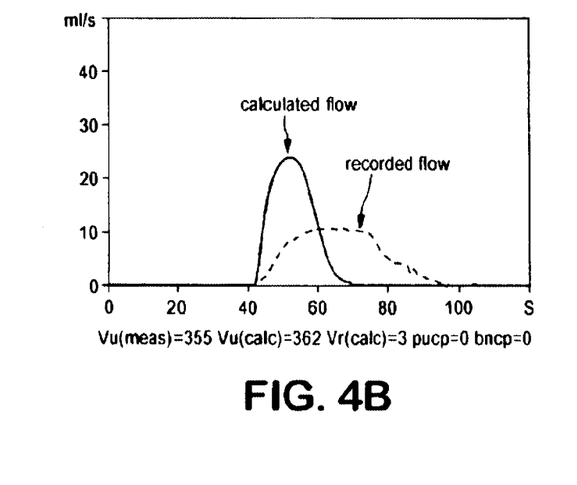
Figure 4C:
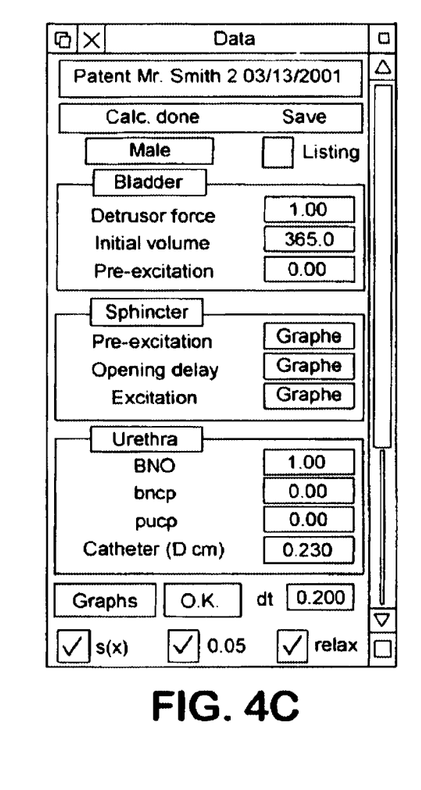
Figure 5A:
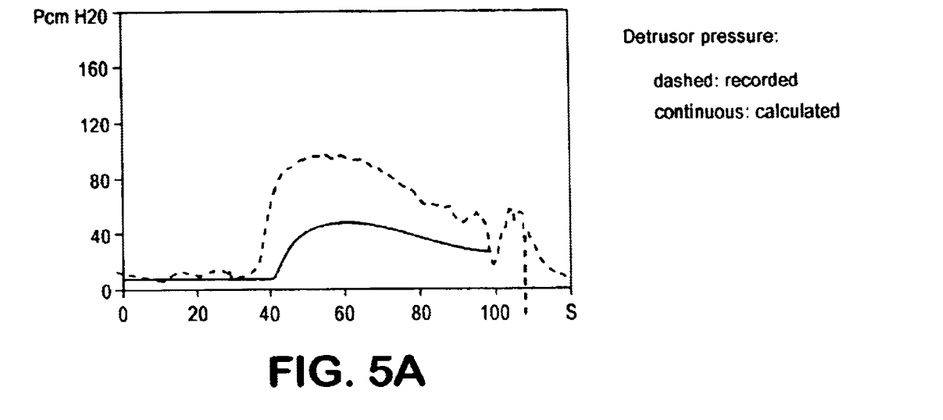
FIGS. 5A and B show graphs of measured detrusor pressure (5A) and flow rate (5B) with modified theoretical curves superimposed.
Figure 5B:
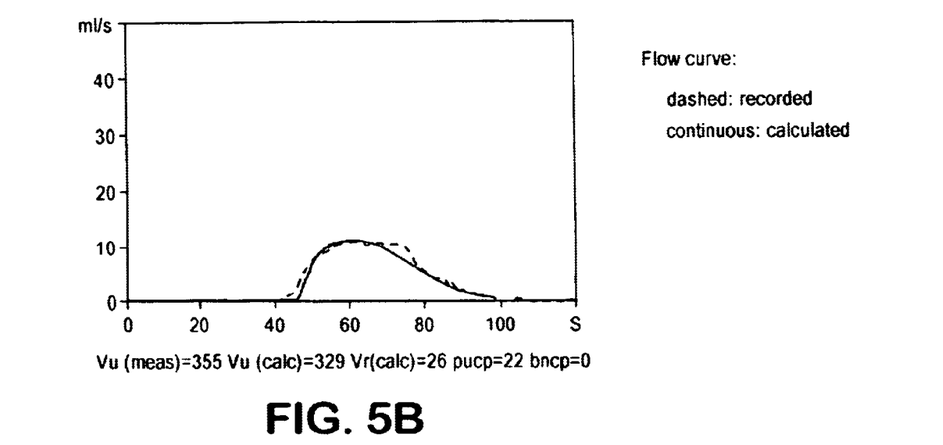

FIG. 4 shows the measured curves from FIGS. 2 and 3 with theoretical curves for detrusor pressure and flow rate resulting from standard parameters for a healthy individual superimposed thereon. In addition to the display of the curves, FIG. 4 shows the window which provides a means for entry of values to be used in refining the calculations for the theoretical curves. By changing these values which are determined to correspond to physiological parameters that produce specific results in urodynamics, the theoretical curves can be recalculated and manipulated to match the measured curves thereby providing an indication of the cause of the values producing the measured curves without resorting to invasive investigations of the patient. For example, in FIG. 4, the urethral catheter diameter is specified as 0.23 cm and the initial volume of the bladder is 355 ml. Beginning with the simple hypothesis that there is no obstruction, i.e., bladder neck counter-pressure=prostatic urethra counter-pressure =0, and that normal excitations are present, the program is commanded to make the calculation to produce the theoretical flow rate and detrusor pressure curves which appear superimposed on the measured curves.

As is evident from FIG. 4, the initial theoretical curves are significantly different from the measured curves. Accordingly, the values used in calculating the theoretical curves are altered and the curves are recalculated. In the present example, an assumption is made that a prostatic obstruction exists and a search is made for a prostatic urethra compressive parameter that fits the flow rate curve. In this instance a value of 22 cm $H_2O$ is applied and the curves recalculated to those shown in FIG. 5. While the flow rate curves fit very well, the theoretical pressure curve is only about half the measured pressure, a finding that indicates the contractile force of the detrusor is stronger than normal which results when the number or diameter of the contractile fibers is unusually high.

Figure 6A:
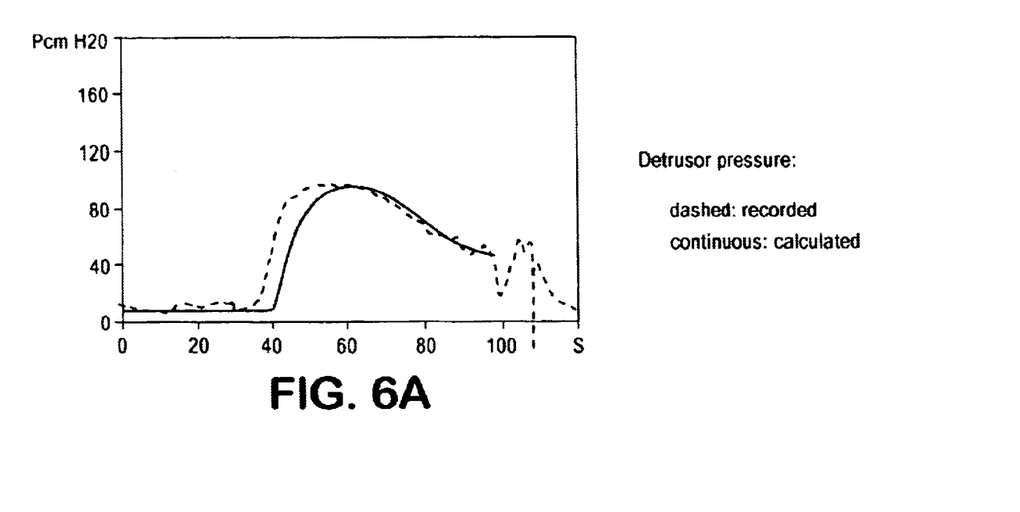
FIGS. 6A and B show graphs of measured detrusor pressure (6A) and flow rate (6B) with further modified theoretical curves superimposed.
Figure 6B:
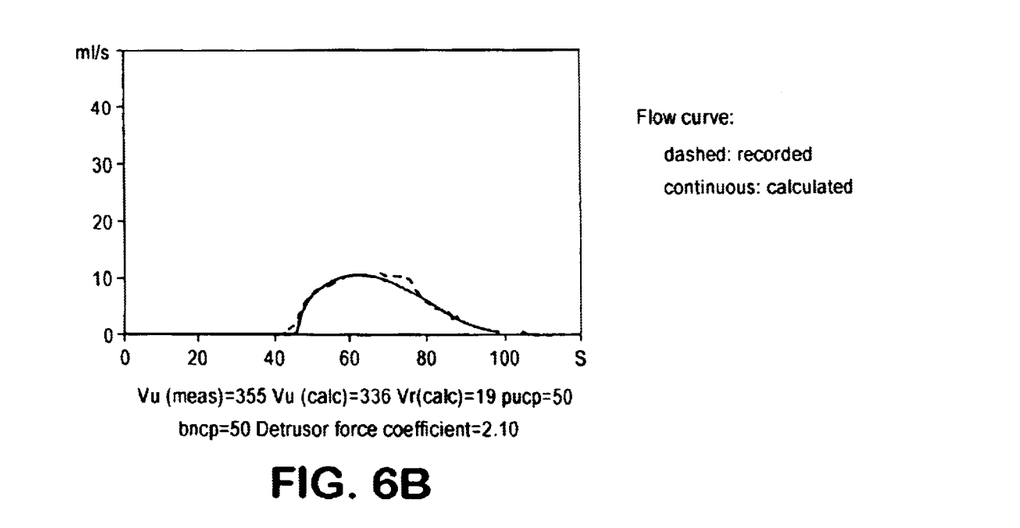

Based on this assumption, a determination is made as to how much higher the number or diameter of contractile fibers would have to be. FIG. 6 shows the best values of prostatic compression and detrusor force coefficient which provide the best fit for both the measured flow rate and measured pressure. The values now applied to the calculations to obtain the theoretical curves are a prostatic pressure of 50 cm $H_2O$ and a detrusor force coefficient of 2.1.

Figure 7A:
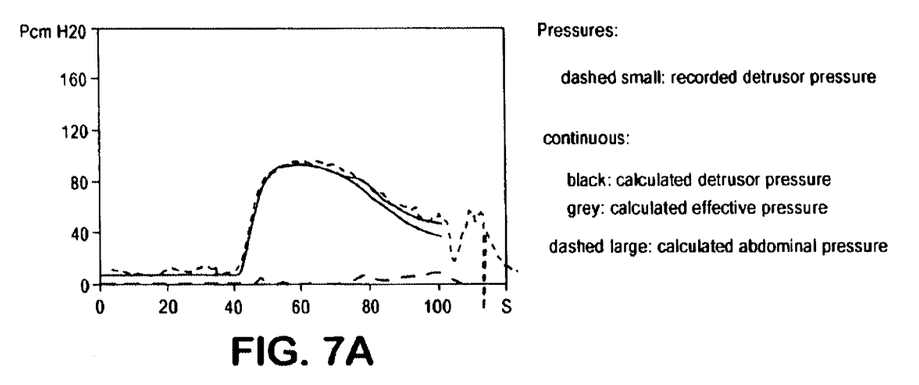
FIGS. 7A and B show graphs of measured detrusor pressure (7A) and flow rate (7B) with final modified theoretical curves superimposed.
Figure 7B:
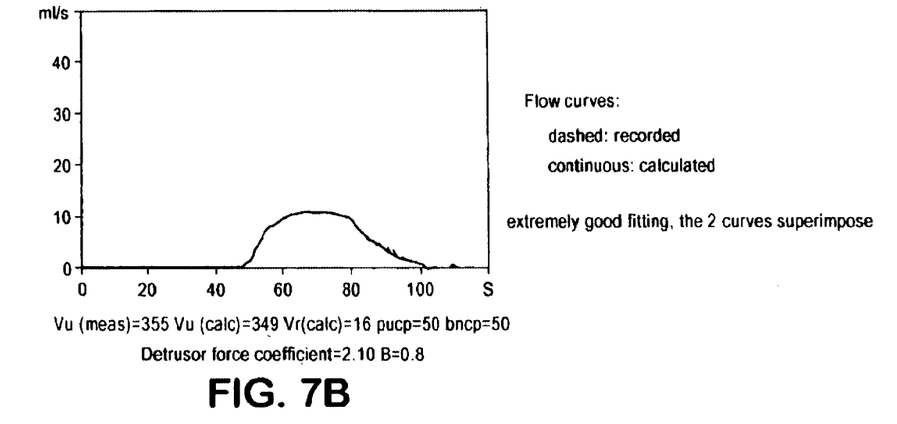

The theoretical curves for pressure and flow rate are now seen to fit the measured curves except for a time delay of about 5 seconds at the beginning of the curves. This delay is characteristic of a tightening of the bladder neck when the detrusor contracts. Accordingly, a detrusor-bladder neck coupling coefficient B=0.80 is added to the calculations and the result is seen in the comparison curves of FIG. 7.

Fine tuning of the calculations for the theoretical curves is made by small corrections of the detrusor excitation value and abdominal pushes to account for any small discrepancies between the theoretical curves and the measured curves.

The present method provides hitherto unavailable means for the evaluation of small discrepancies in the comparison curves. In addition, it is now possible to evaluate, in vivo, changes in bladder structure that are induced by a bladder outlet obstruction. Similarly, the suspected phenomenon of bladder neck contraction can now be evaluated without cineradiography.

The method has a wide field of use in that it may be applied at the research level to detect phenomena induced by disease or at the clinical level as a quantified help to diagnosis and as a detector of rare abnormalities. It can be used to follow the action of treatment regimes, such as chemical treatments and to follow the evolution of patients after a surgical operation.

Urodynamic examinations are always made with the implicit hope to compare the measured curves to theoretical predictions resulting from a knowledge of the lower urinary tract system. Although the theoretical description of the system is known, most of the equations can be found in "Urodynamics: The Mechanics And The Urodynamic Of The Lower Urinary Tract" Adam Hilger, 1980, Griffiths, the mathematical tools necessary to integrate this large set of equations and to discuss and apply the numerical values was lacking.

The method presented herein permits one to overcome this deficiency and, a) take into account the initial viscoelastic state and the detrusor force coefficient, b) use more refined laws for the urethral elasticity and urethral geometry and to take into account the perturbations due to the presence of a urethral catheter, c) calculate an exact solution of the hydrodynamic equations, and d) give a time depending description of sphincter and detrusor excitations.

Figure 11A:
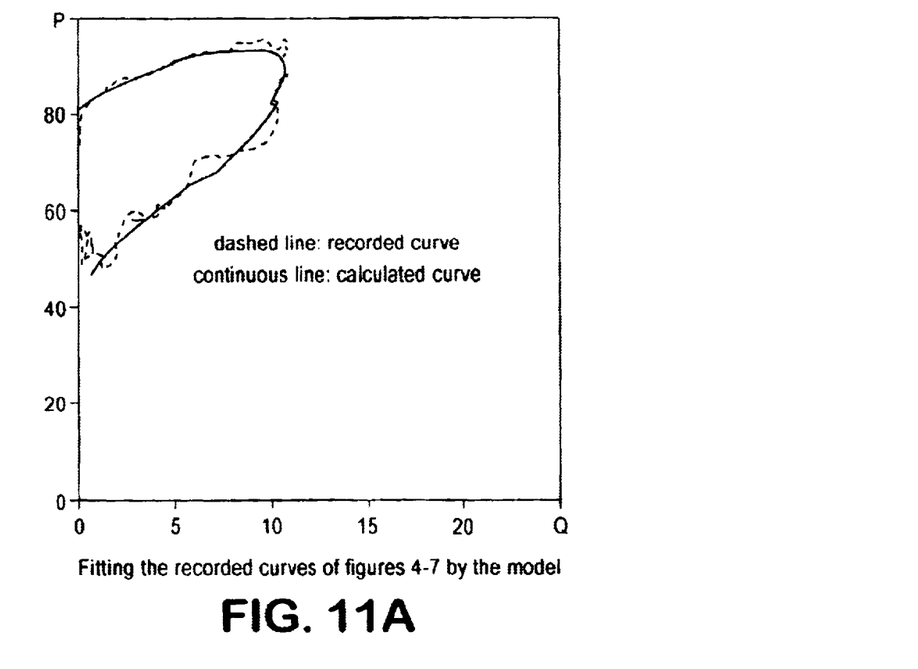
FIGS. 11A and B illustrate the fitting of recorded data using the method of the present invention.
Figure 11B:
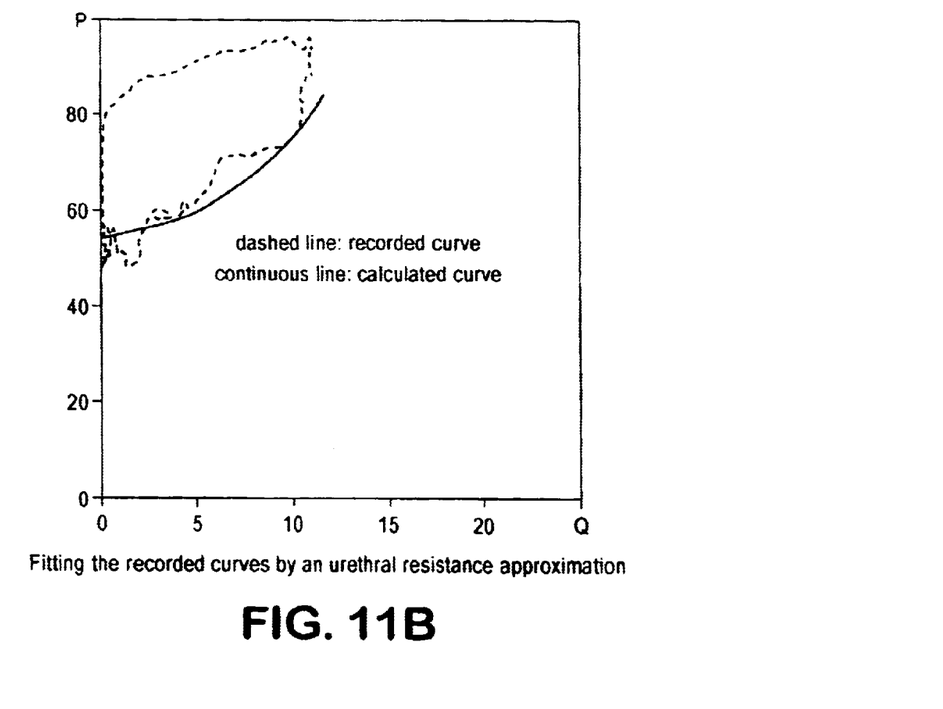

Prior attempts to fit the recorded curves by theoretical ones use very crude approximations. The most common consists of replacing all the hydrodynamic equations by a urethral resistance. Often, the time dependent curves P(t) and Q(t) are not considered and only the flow vs. pressure curve P(Q) is used. A urethral resistance would lead to a parabolic law $P=Po+R.Q^2$, recorded curves being roughly parabolic for some time. FIG. 11 shows how the method of the present invention can produce a calculated curve that more precisely fits a recorded curve P(Q) for the patient whose Q(t) and P(t) recordings are presented in FIG. 7. In contrast, a curve calculated from the parabolic law using a urethral resistance approximation does not fit the recorded curve. In addition, prior computer assisted devices and methods that obtain a parabolic fitting cannot analyze phenomena linked to a urethral obstruction such as detrusor muscle or nervous control abnormalities. Nor can they distinguish between a urethral obstruction requiring surgery and an impaired detrusor, which does not require surgery.

In conclusion, the present invention provides a method for identifying and analyzing the condition of the lower urinary tract which permits an accurate determination of the condition of a patient without resort to non-invasive techniques.

In conclusion, the present invention provides a method for identifying and analyzing the condition of the lower urinary tract which permits an accurate determination of the condition of a patient without resort to non-invasive techniques:

What is claimed is:

1. A method for non-invasively identifying the functional status of the lower urinary tract comprising:

recording urodynamic and pressure data of a patient during micturition, plotting said recorded data as curves, calculating theoretical models based on standard physiological parameters and plotting said models as curves, applying said theoretical model curves to said recorded data curves, and modifying values of said theoretical models to bring said theoretical model curves into coincidence with said recorded data curves, whereby physiological parameters affecting micturition are determined according to the values modified and the degree of modification necessary to achieve coincidence.

2. The method of claim 1 wherein said calculations are performed using a computer and software designed to apply supersonic flow equations to the calculation of urodynamic parameters.

3. The method of claim 2 wherein said recorded data comprises intravesical pressure, abdominal pressure, detrusor pressure, flow rate and volume.

4. The method of claim 3 wherein said theoretical models are based on characteristics describing parameters corresponding to a healthy urinary tract, wherein said parameters comprise:

a) geometry and contractile, elastic and visco-elastic properties of the bladder, b) geometry and contractile and elastic properties of the bladder neck, c) geometry and elastic properties of the urethra from the bladder neck to the urinary meatus, d) geometry of the contractile properties of the urinary sphincters, e) variation over time of the nervous excitation of the detrusor, f) variation over time of the nervous excitation of the sphincters, and g) the effect of the perineal muscles.

5. The method of claim 4 wherein curves for the theoretical models are superimposed over recorded data curves on a computer display screen for direct comparison.

6. The method of claim 5 wherein the theoretical models and displayed curves therefor are directly recalculated and manipulated by entry into the computer of alternative values for said parameters whereby said computer makes said recalculation and displays revised curves relative to said recorded data curves for direct comparison and whereby said revised curves provide a direct visual indication of a physiological condition responsible for said recorded data and a determination of actual urinary tract status.

7. A method for non-invasive evaluation of the functional status of the human lower urinary tract comprising performing a direct comparison of recorded urodynamic data and theoretical models describing an ideal urinary tract using a computer and operating software to produce said theoretical models from supersonic flow calculations based on parameters consistent with characteristics for a healthy human urinary tract whereby the difference between said recorded data and said theoretical models is indicative of the functional status of said urinary tract.

8. The method of claim 7 wherein said parameters comprise:

a) geometry and contractile, elastic and visco-elastic properties of the bladder, b) geometry and contractile and elastic properties of the bladder neck, c) geometry and elastic properties of the urethra from the bladder neck to the urinary meatus, d) geometry of the contractile properties of the urinary sphincters, e) variation over time of the nervous excitation of the detrusor, f) variation over time of the nervous excitation of the sphincters, and g) the effect of the perineal muscles.

9. The method of claim 8 further comprising displaying recorded urodynamic data and theoretical models on a computer display screen as superimposed curves.

10. The method of claim 9 further comprising manipulating said theoretical models to bring said superimposed curves into coincidence whereby the specific values manipulated and the degree of manipulation are indicative of a physiological condition affecting the urinary tract and micturition.

* * * * *